United States Patent

Ganz

[11] Patent Number: 4,666,448
[45] Date of Patent: May 19, 1987

[54] HIP JOINT SOCKET FOR CEMENT-FREE ANCHORING IN THE PELVIS

[75] Inventor: Reinhold Ganz, Gümligen, Switzerland

[73] Assignee: Protek AG, Bern, Switzerland

[21] Appl. No.: 672,289

[22] Filed: Nov. 16, 1984

[30] Foreign Application Priority Data

Nov. 18, 1983 [DE] Fed. Rep. of Germany ....... 3341723

[51] Int. Cl.$^4$ .............................................. A61F 2/34
[52] U.S. Cl. ..................................................... 623/22
[58] Field of Search ........................ 3/1.9, 1.91, 1.912, 3/1.913; 128/92 C, 92 CA; 623/16, 17, 18, 19, 20, 21, 22, 23

[56] References Cited

U.S. PATENT DOCUMENTS

| 4,159,544 | 7/1979 | Termanini | 3/1.912 |
| 4,385,405 | 5/1983 | Teinturier | 623/22 |
| 4,450,592 | 5/1984 | Niederer et al. | 623/22 |

FOREIGN PATENT DOCUMENTS 2358159 7/1974 Fed. Rep. of Germany .
7500535 7/1975 Fed. Rep. of Germany .

OTHER PUBLICATIONS

Aesculap 113-C10 77/4 p. 12, "Total-Endoprothesen fur das Huftgelenk".
MR-Cementless Hip Prosthesis, Mecron med. Produkte GmbH, Berlin, Jun. 21, 1985.

Primary Examiner—Richard J. Apley
Assistant Examiner—David J. Isabella
Attorney, Agent, or Firm—Toren, McGeady and Goldberg

[57] ABSTRACT

A hip joint socket for cement-free anchoring in the pelvis includes a socket member with a hemispherical exterior surface which is flattened at its apex region and a socket which is spherical-symmetrical relative to the rotational axis of symmetry of the exterior surface.

The exterior surface of the socket member projects rimless above the equatorial plane of the socket and has the form of a regular cylinder beyond the equatorial plane.

9 Claims, 2 Drawing Figures

HIP JOINT SOCKET FOR CEMENT-FREE ANCHORING IN THE PELVIS

BACKGROUND OF THE INVENTION

The present invention is directed to a hip joint socket for cement-free anchoring in the pelvis, made of plastic material and it includes a socket member with a hemispherical exterior surface which is flattened at its apex region and a socket which is spherical-symmetrical relative to the rotational axis of symmetry of said exterior surface.

For artificial hip joint sockets there is the general requirement for dimensioning the socket to be implanted as a foreign body into the pelvis as small as possible for two reasons. First for limiting the inevitable losses of bone substance and second for reducing the volume of the artifical foreign body to the absolute minimum.

Taking into account these arguments sockets with an approximatively hemispherical shape are to be preferred to those with a conical or cylindrical (note Swiss Pat. No. 566,128) basic shape. Hip joint sockets of the aforementioned type are therefore known for implantation into small, shallow acetabula (note the leaflets from ALLO PRO "Die Hüftgelenk-Endoprothese, System Weber-Stühmer" of 1977 and from AESCULAP 113-C 10 77/4, page 12 "Total-Endoprothesen für das Hüftgelenk").

All these sockets are designed for anchoring with the aid of bone cement. They are not suitable for cement-free implantation having neither an adequate structure of the outer surface, e.g. an exterior thread, nor anchoring pegs or screws for a cement-free fixation, nor can they be clamped into the pelvis.

With a cementfree anchoring the implanted socket is held with a certain prestress in the pelvis. The clamping of the socket member occurs thereby at the lateral surface, i.e. at the equatorial regions. With the aforementioned prior art sockets the clamping effect is prevented due to the flange type rim of the socket.

Furthermore the fixation by clamping is insufficient with these known sockets because theoretically it takes place only along a line in the equatorial plane.

SUMMARY OF THE INVENTION

Therefore it is the primary object of the present invention to provide a hip joint socket with a flattened apex region suitable for cement-free anchoring by equatorial clamping.

In accordance with the present invention the exterior surface of the socket member projects rimless, i.e., without a collar, edge or flange coming into contact with the pelvis, above the equatorial plane of the socket and has the form of a regular cylinder beyond the equatorial plane.

The flattening in the apex region and the rimless shape of the exterior surface of the socket member made of a plastics material allow to implant the socket "deeply" into the prepared pelvis, whereby the cylindrical projection increases the clamping effect by enlarging the contact line to a contact area, because the spherical cutter (grater) produces a cylindrical contour of the cutting as soon as it penetrates into the bone beyond its equatorial plane.

If necessary the exterior surface of the socket member may be provided with a structure, preferably with a ribbed structure which enhances the ingrowth of bone substance. The socket member is made of a plastics material preferably of polyethylene of the classification HDPE (high density polyethylene) and UHMW (ultrahigh molecular weight).

The various features of novelty which characterize the invention are pointed out with particularity in the claims annexed to and forming a part of this disclosure. For a better understanding of the invention, its operating advantages and specific objects attained by its use, reference should be had to the accompanying drawing and descriptive matter in which are illustrated and described preferred embodiments of the invention.

DETAILED DESCRIPTION OF THE INVENTION

Figure 1:
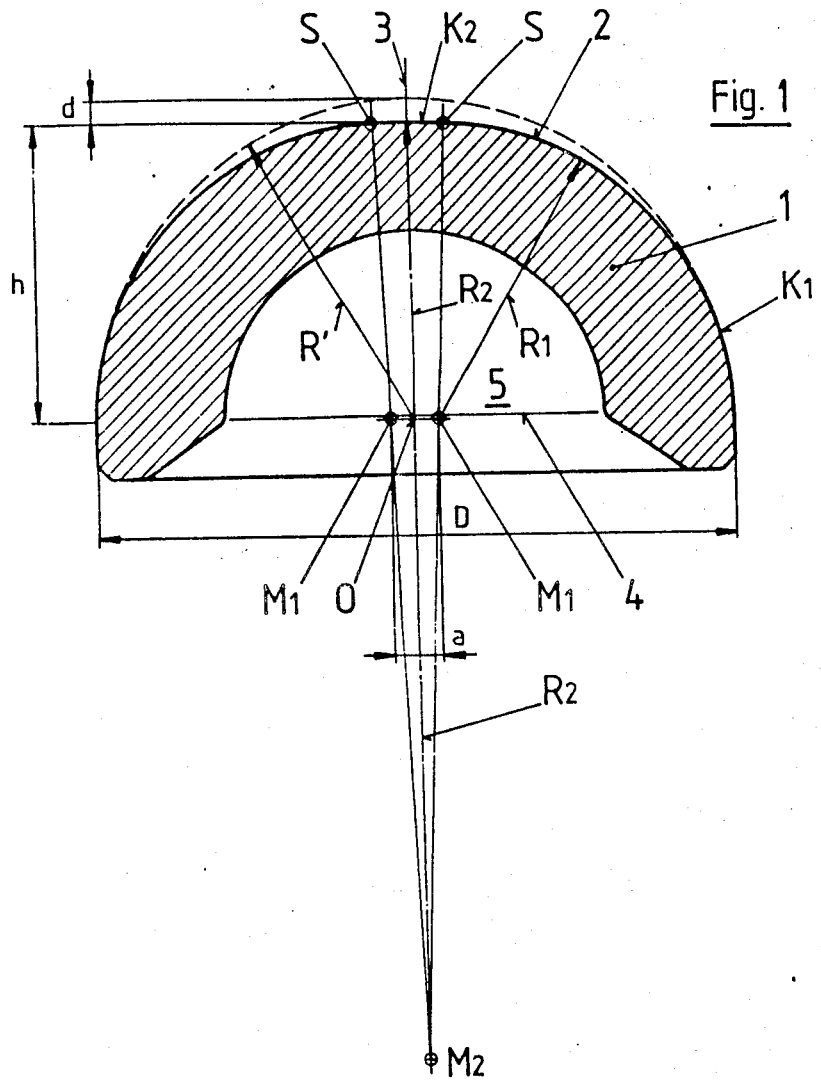
FIG. 1 is a section through the rotational axis of symmetry of the hip joint socket of the present invention.

As illustrated in FIG. 1 the exterior shape of the socket member 1 of the hip joint socket is formed as a rotational solid generated by rotation of the profile 2 around the rotational axis of symmetry 3; the socket 5 is formed by a hemispherical cavity which is also symmetrical with regard to the rotational axis of symmetry 3.

Figure 2:
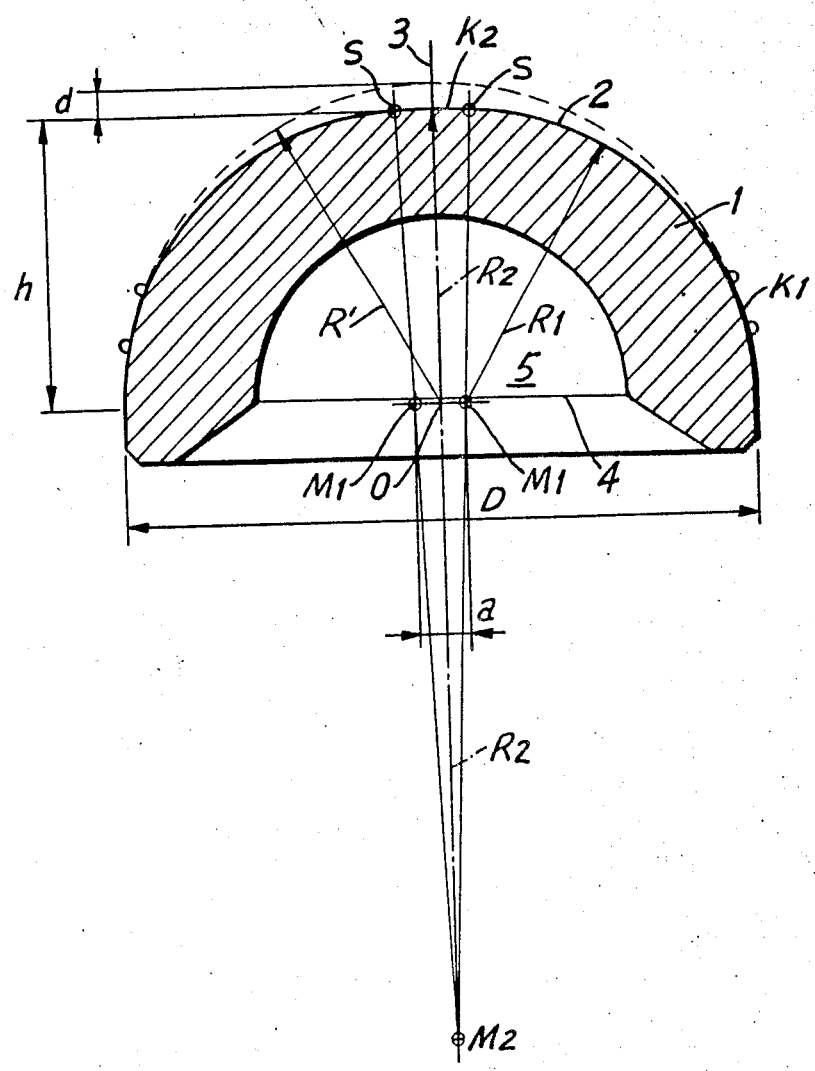
FIG. 2 is a section of a socket similar to FIG. 1 having a ribbed structure on its extrior surface.

FIG. 2 shows a structure the same as FIG. 1, except with a ribbed exterior surface.

The rimless socket member 1 has a diameter D measured in its equatorial plane 4. This diameter D is also the generating diameter of the exterior surface of the socket, which is located beyond the equatorial plane 4.

The basis for the exterior surface of the socket member 1 is formed by a sphere with the radius $R'=D/2$; this semispherical surface is flattened at its apex region by the amount $d=R'-h$.

Therefore the profile 2 of the socket member 1 is composed by at least three different curves. Adjacent to the afore-mentioned regular cylindrical portion beyond the equatorial plane 4 the profile 2 is formed—from the equatorial plane—by two arcs of circles $K_1$ and $K_2$, of which one has the radius $R_1$ which can be calculated in a first approximation to be $R_1=R'-d$.

Symmetrical to the mirror plane of the socket member 1, containing the rotational axis of symmetry 3, the centers $M_1$ of the arcs of circles $K_1$ for the equatorial regions of the profile 2 are located in the equatorial plane 4. The distance between the two centers $M_1$ is a and may vary, according to the preferred embodiment shown in the FIG., from 1 to 5 mm.

In the preferred embodiment the profile 2 extends from the equatorial plane 4 to the points S according to the arcs of circles $K_1$. The arc between the two points S is formed by a second arc of circle $K_2$ with the radius $R_2$ which is approximately 3 times longer than the radius $R_1$. The center $M_2$ of the arc of circle $K_2$ is located on the rotational axis of symmetry 3.

For the dimensioning of the hip joint socket the diameter D and the "flattening" d are given as basic parameters, allowing within certain limits to choose the radii $R_1$ and $R_2$, determining the distance a.

It will thus be seen that the objects set forth above, among those made apparent from the preceding description, are efficiently attained, and, since certain changes may be made in the above constructions without departing from the scope of the invention, it is intended that all matter contained in the above description or shown in the accompanying drawing be interpreted as illustrative and not in a limiting sense.

It is also to be understood that the following claims are intended to cover all of the generic and specific features of the invention herein described.

What is claimed as new and desired to be secured by Letters Patent of the United States is:

1. A hip joint socket for cementfree pre-stressed anchoring in a prepared cavity in the pelvis, made of plastic material, comprising a socket member with a hemispherical exterior surface which is flattened at its apex region and a socket which is spherical-symmetrical relative to the rotational axis of symmetry of said exterior surface, wherein the improvement comprises that said exterior surface of said socket member projects rimless beyond the equatorial plane of said socket with extending tangent lines forming a regular cylinder beyond said equatorial plane thereby increasing the clamping effect of said socket within the pelvis by the enlarged area of surface contact of the exterior surface near the equatorial plane of said socket and that said flattened apex region is restorable at least approximately to a hemisphere by pre-stressing the equatorial region of said socket member upon insertion into said cavity, said cavity having a slightly smaller diameter than said socket.

2. A hip joint socket, as set forth in claim 1, wherein the profile of said exterior surface of said socket member is formed by at least two types of arcs of circles $K_1$ and $K_2$ of which one of them ($K_2$) constitutes said profile of said exterior surface is said apex region of said socket member with arcs $K_1$ extending to opposite sides thereof, said arc $K_2$ having its center $M_2$ on said rotational axis of symmetry of said outer surface with the radius $R_2$ which is at least 2 times longer than the radii $R_1$ of said second arcs $K_1$, said arcs $K_1$ having centers located on both sides of said rotational axis of symmetry in said equatorial plane of said socket and spaced apart a distance a.

3. A hip joint socket, as set forth in claim 2, wherein said radius $R_2$ of the said arc of said circle $K_2$ forming said apex region of said profile of said outer surface is 2 to 4 times longer than said radii $R_1$ of said arcs $K_1$.

4. A hip joint socket, as set forth in claim 2 or 3, wherein said distance a of said centers $M_1$ of said arcs of circles $K_1$ forming said equatorial regions of said profile of said outer surface is between 1 and 5 mm.

5. A hip joint socket according to claim 1, 2 or 3, wherein said exterior surface of said socket member has a ribbed structure.

6. A hip joint socket according to claim 4, wherein said exterior surface of said socket member has a ribbed structure.

7. A hip joint socket according to claim 2, wherein said radius $R_2$ is 3 times longer than said radii $R_1$.

8. A hip joint socket according to claim 2, wherein said radius $R_2$ is between 2.5 and 3.5 times longer than said radii $R_1$.

9. A hip joint socket for cement-free pre-stressed anchoring in a prepared cavity in the pelvis, made of plastic material, comprising a socket member with a hemispherical exterior surface which is flattened at its apex region and a socket which is spherical-symmetrical relative to the rotational axis of symmetry of said exterior surface, wherein the improvement comprises that said exterior surface of said socket member projects rimless beyond the equatorial plane of said socket thereby increasing clamping effect of said socket within the pelvis by the enlarged area of surface contact of the exterior surface near the equatorial plane of said socket and that said flattened apex region is restorable at least approximately to a hemisphere by pre-stressing the equatorial region of said socket member upon insertion into said cavity, said cavity having a slightly larger diameter than said socket.

* * * * *